United States Patent [19]
Adachi et al.

[11] Patent Number: 4,857,645
[45] Date of Patent: Aug. 15, 1989

[54] PROCESS FOR INTRODUCING A THIOCARBOXYLIC ESTER GROUP AT THE ORTHOPOSITION OF PHENOLS OR PHENYLAMINES

[75] Inventors: Makoto Adachi, Nara; Hiromu Matsumura; Tsutomu Sugasawa, both of Hyogo, all of Japan

[73] Assignee: Shionogi & Co., Ltd., Osaka, Japan

[21] Appl. No.: 116,792

[22] Filed: Nov. 5, 1987

[30] Foreign Application Priority Data

Nov. 6, 1986 [JP] Japan ................................. 61-264658

[51] Int. Cl.$^4$ .................. C07D 241/36; C07D 471/00; C07D 487/00; C07D 211/56
[52] U.S. Cl. ........................................ 544/349; 544/35; 558/250; 558/252; 558/257; 546/244; 548/530; 549/513
[58] Field of Search ............... 558/250, 252, 257; 546/244; 548/530; 544/35, 349; 549/571

[56] References Cited

U.S. PATENT DOCUMENTS

| | | | |
|---|---|---|---|
| 3,231,598 | 1/1966 | Berezin et al. | 558/250 |
| 3,338,947 | 8/1967 | Berezin et al. | 558/257 |
| 3,492,375 | 1/1970 | Gruber et al. | 558/252 |
| 3,929,852 | 12/1975 | Kydonieus et al. | 558/252 |
| 3,933,813 | 1/1976 | Beschke et al. | 558/250 |
| 4,165,333 | 8/1979 | Kline | 558/257 |
| 4,600,576 | 7/1986 | Pittet et al. | 558/250 |

FOREIGN PATENT DOCUMENTS 0266849  5/1988  European Pat. Off. ............ 558/252

OTHER PUBLICATIONS

W. Theilheimer: "Synthetic Methods of Organic Chemistry", vol. 27, 1973, p. 273, S. Karger, Basel, CH, p. 273, par. 597.
Journal of the American Chemical Society, vol. 45, July 1923, pgs. 1744–1752, R. J. Kaufmann et al.; "Production of Imido Thiol Esters by the Condensation of Thiocyanates with Resorcinol or Phloroglucinol", pgs. 1744–1745.

*Primary Examiner*—Patrick P. Garvin
*Assistant Examiner*—E. D. Irzinski
*Attorney, Agent, or Firm*—Birch, Stewart, Kolasch & Birch

[57] ABSTRACT

A process for introducing thiocarboxylic ester at orthoposition of phenols or phenylamines which comprises reacting a phenyl compound having group or optionally substituted amino or cyclic amino group, of which at least one ortho-position is vacant, with $C_1$–$C_5$ alkyl thiocyanate, $C_7$–$C_{13}$ aralkyl thiocyanate or $C_6$–$C_{12}$ aryl thiocyanate in the presence of a boron trihalide and hydrolyzing the resultant product under acidic conditions is provided, and said process is useful in the synthesis of medicinals, pesticides and dyes.

9 Claims, No Drawings

PROCESS FOR INTRODUCING A THIOCARBOXYLIC ESTER GROUP AT THE ORTHOPOSITION OF PHENOLS OR PHENYLAMINES

BACKGROUND OF THE INVENTION

The present invention relates to a process for introducing a thiocarboxylic ester group at the ortho-position of phenols or phenylamines. More particularly, this invention is directed to a process for introducing a thiocarboxylic ester group at the orth-position of phenols or phenylamines which have been found to be useful in the systhesis of medicinals, pesticides and dyes.

The undermentioned reactions are known.

(a) R. J. Kaufmann et al., J. Am. Chem. Soc. 45 1744 (1923)

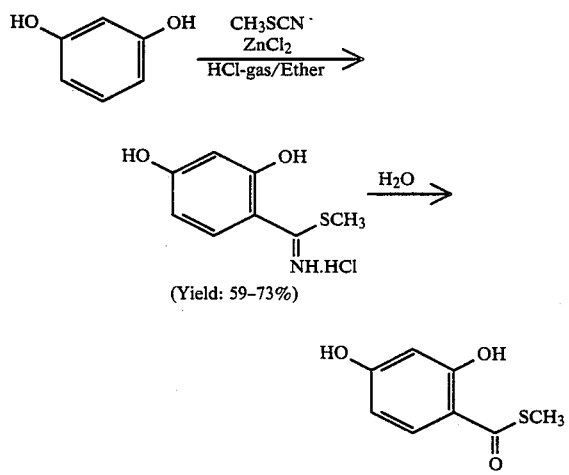

This reaction gives an objective compound only with polyhydric phenol; when simple phenols are applied to this reaction, no ortho-substituted product is obtained.

(b) Dow Chemical, U.S. Pat. Nos. 3338947 and 3377372

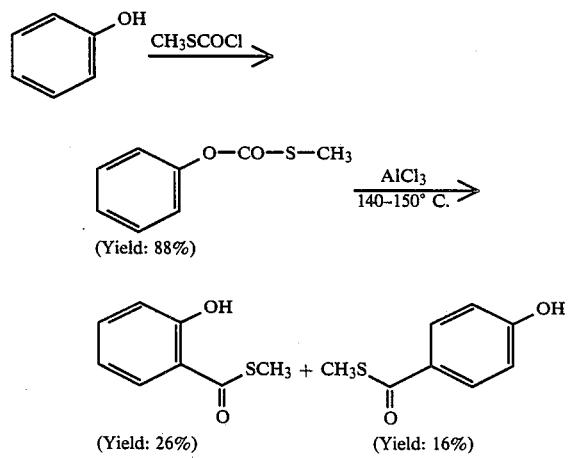

(c) S. Ohta et al., Tetrahedron Lett., 22 3245 (1981)

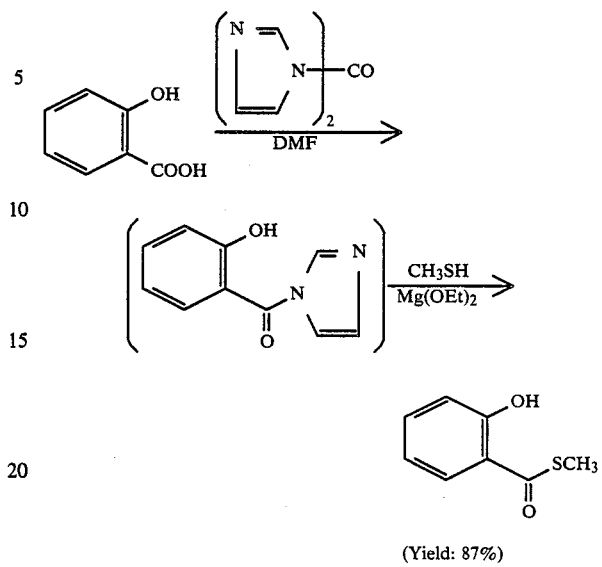

These conventional reactions do not always give satisfactory yields, and ortho-substituted thiobenzoic acid ester derivatives having other desirable substituents at any desired position are not obtained.

SUMMARY OF THE INVENTION

According to the present invention, there is provided a process for intoducing a thiocarboxylic ester group at the ortho-position of phenols or phenylamines which comprises reacting a phenyl compound a hydroxy group or optionally substituted amino or cyclic amino group, of which at least one ortho-position is vacant, with $C_1$–$C_5$ alkyl thiocyanate or $C_6$–$C_{12}$ aryl thiocyanate in the presence of a boron trihalogenide and hydrolyzing the resultant product under acidic conditions.

The said reaction is summarized by the undermentioned scheme.

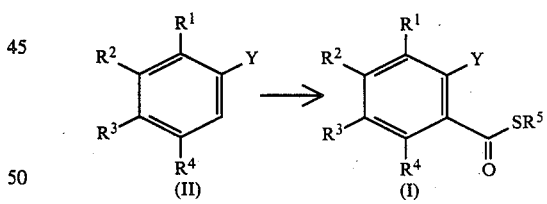

(wherein $R^1$, $R^2$, $R^3$ and $R^4$ each is hydrogen, halogen, $C_1$–$C_5$ alkyl, $C_1$–$C_5$ alkoxy, $C_1$–$C_5$ alkylthio, $C_6$–$C_{12}$ aryloxy, $C_7$–$C_{15}$ aralkyl, $C_7$–$C_{15}$ aralkoxy or $C_1$–$C_{10}$ acylamino, or ($R^1$ and $R^2$) or ($R^2$ and $R^3$) each taken together form a condensed benzene ring optionally substituted by halogen, $C_1$–$C_5$ alkyl or $C_1$–$C_5$ alkoxy, Y is hydroxy, amino or -NHR, and R is $C_1$–$C_5$ alkyl, $C_7$–$C_{15}$ aralkyl, $C_6$–$C_{12}$ aryl or N-(methyl- or benzyl-substituted)aza($C_3$–$C_7$ cycloalkyl), and $R^5$ is $C_1$–$C_5$ alkyl, $C_7$–$C_{13}$ aralkyl, $C_6$–$C_{12}$ aryl.)

The said phenyl compound (II) consists of two types, A type and B type. In these cases, the reactions proceed through the process as follows:

A type

-continued

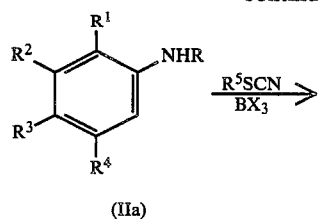

(IIa)

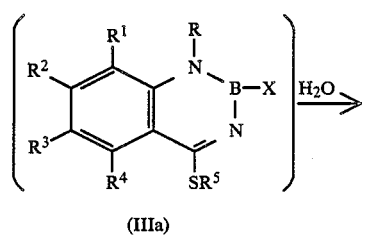

(IIIa)

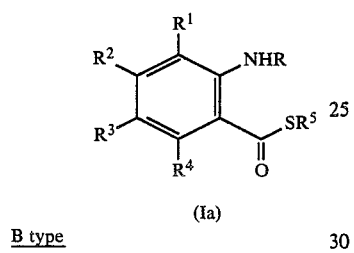

(Ia)

B type

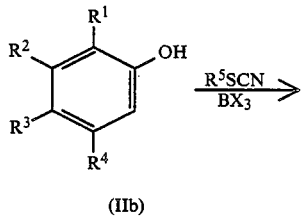

(IIb)

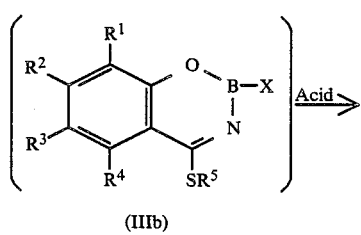

(IIIb)

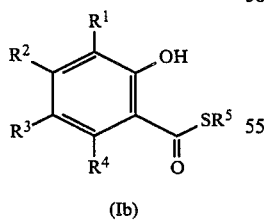

(Ib)

(wherein $R^1$, $R^2$, $R^3$, $R^4$ and R each has the same meaning as defined above, and X is halogen (Cl or Br), $R^5$ is $C_1$–$C_5$ alkyl, $C_7$–$C_{13}$ aralkyl or $C_6$–$C_{12}$ aryl).

Further the A type (IIa) additionally includes the C type (IIc) and the D type (IId). When R and $R^1$ of the A type (IIa) taken together form a 5- or 6-membered heterocycle, the reactions of these compounds are illustrated as follows:

C type

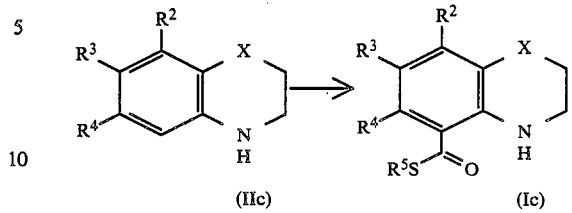

(IIc)        (Ic)

D type

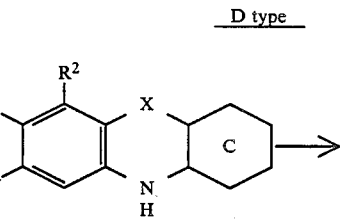

(IId)

(Id)

(wherein the ring C is a benzene, pyridine or cyclohexane ring, each of which is optionally substituted by halogen, $C_1$–$C_5$ alkyl or $C_1$–$C_5$ alkoxy, X is a single bond, O, S or N(methyl)-, and $R^2$, $R^3$, $R^4$ and $R^5$ each has the same meaning as defined above).

The terms used in the above definitions are illustratively explained below.

The term "$C_1$–$C_5$ alkyl" herein employed refers to a straight or branched saturated aliphatic hydrocarbon radical such as methyl, ethyl, n-propyl, n-butyl, isobutyl, sec-butyl, tert-butyl, n-pentyl, isopentyl, sec-pentyl, tert-pentyl and neo-pentyl.

The term "$C_1$–$C_5$ alkoxy" represents methoxy, ethoxy, n-propoxy, isopropoxy, n-butoxy, isobutoxy, sec-butoxy, tert-butoxy, neo-pentyloxy and sec-pentyloxy.

The term "$C_1$–$C_5$ alkylthio" represents methylthio, ethylthio, propylthio, isopropylthio, butylthio, pentylthio and isopentylthio.

The term "$C_6$–$C_{12}$ aryl" means phenyl, tolyl, xylyl, naphthyl, pyridyl, thienyl and furyl.

The term "halogen" means chlorine, bromine, flourine and iodine.

The term "$C_6$–$C_{12}$ aryloxy" means phenoxy, naphthoxy, pyridyloxy and tolyloxy.

The term "$C_7$–$C_{15}$ aralkyl" includes benzyl, phenethyl, phenylpropyl, phenylbutyl, naphthylmethyl and naphthylpropyl.

The term "$C_7$–$C_{15}$ aralkoxy" includes benzyloxy, phenethyloxy, phenylpropyloxy, phenylbutyloxy and naphthylmethoxy.

The term "$C_1$–$C_{10}$ acylamino" includes formylamino, acetylamino, propionylamino, butyrylamino, benzoylamino, phenylacetylamino and phenylbutyrylamino.

Moreover, the alkyl, alkoxy, aryl, aryloxy, aralkyl and aralkoxy above mentioned my be optionally substituted by $C_1$-$C_5$ alkyl, $C_1$-$C_5$ alkoxy or halogen.

The boron trihalogenide used in this reaction refers to boron trichloride or boron tribromide.

The thiocyanates usable as one of the other starting materials includes alkyl thiocyanates, aralkyl thiocyanates and aryl thiocyanates, of which hydrocarbon groups may have one or more substitutents selected from alkyl, alkoxy and halogen.

As the thiocyanates used herein, alkyl thiocyanate such as methyl thiocyanate, ethyl thiocyanate, propyl thiocyanate or butyl thiocyanate, aralkyl thiocyanate such as benzyl thiocyanate or phenethyl thiocyanate and aryl thiocyanate such as phenyl thiocyanate or naphthyl thiocyanate are exemplified.

The process for introducing a thiocarboxylic ester group at the ortho-position of the present invention and the starting materials of the A type, B type, C type and D type are explained below in detail.

A type

The phenylamines (IIa) are allowed to react with thiocyanates in the presence of a boron trihalogenide (boron trichloride or boron tribromide) to give boron compounds (IIIa), and the boron compounds (IIIa) is hydrolyzed with water to give the objective compounds (Ia).

The reactions of phenylamines (IIa) with thiocyanates are performed in the presence of a boron trihalogenide in an appropriate inert solvent (e.g. methylene chloride, 1,2-dichloroethane, benzene, toluene, xylene, etc.) at room temperature (1°–30° C.) or from room temperature to about the boiling point of the solvent used. The hydrolysis can be performed in an aqueous solution at ordinary temperature (0°–30° C.) or under heating (30°–100° C.).

B type

The phenols (IIb) are allowed to react with thiocyanates in the presence of a boron trihalogenide (boron trichloride or boron tribromide) to give the boron compounds (IIIb). The reaction of phenols (IIb) with thiocyanates can be performed as described in the A type. The reaction proceeds smoothly, but the yield increases by adding an appropriate Lewis acid (e.g. aluminium chloride, stannic chloride, titanium tetrachloride, etc.). Then the obtained boron compound is hydrolyzed with dilute acid (e.g. hydrochloric acid, sulfulic acid, etc.) to give the objective compound (Ib). The hydrolysis proceeds in a conventional manner. The hydroxy group of the thiocarboxy esters (Ib) obtained in this reaction can be easily subjected to the alkylation with alkyl halides, aryl halides, aralkyl halides, dialkyl sulfates or epihalohydrins in a conventional manner.

C type and D type

The cyclic amines (IIc) and (IId) can be allowed to react with thiocyanates as in the case of phenylamines (IIa).

Presently preferred and practical embodiments of the process of the present invention are illustratively shown in the following working examples, which do not limit the technical scope of the invention.

The abbreviations used in this specification have the following meanings.

| | | |
|---|---|---|
| Me: methyl | n-Pr: n-propyl | n-Bu: n-butyl |
| Et: ethyl | i-Pr: isopropyl | Ph: phenyl |
| OMe: methoxy | SMe: methylthio | $CH_2Ph$: benzyl |
| BN: benzene | DM: methylene chloride | |
| TL: toluene | DE: 1,2-dichloroethane | |
| DMF: dimethylformamide | | |

EXAMPLE 1

To a solution of 1.07 g of N-methylaniline in 10 ml of toluene was added 5.5 ml of a solution of 2.02M boron trichloride—toluene under ice-cooling, and the mixture was refluxed with heating on an oil bath for 1 hr. and concentrated under atomspheric pressure. The residue was cooled with ice-water, mixed with 1 ml of methyl thiocyanate and stirred for 30 min. under ice-cooling and 2.25 hr. at room temperature. The reaction mixture was mixed with 20 ml of water and heated under reflux for 30 min. The product was extracted with toluene, dried over anhydrous magnesium sulfate, concentrated and subjected to chromatography of silica gel. The eluate with toluene was concentrated to give 1.62 g of N-methylthioanthranilic acid S-methyl ester as a pale yellow oil.

Yield: 90%.

IR: 3360, 1626 $cm^{-1}$.

EXAMPLE 2-15

Using the undermentioned starting materials (IIa), the reactions were performed in the same manner as in Example 1, whereby the corresponding objective compounds (Ia) were obtained.

The results are shown in Table 1.

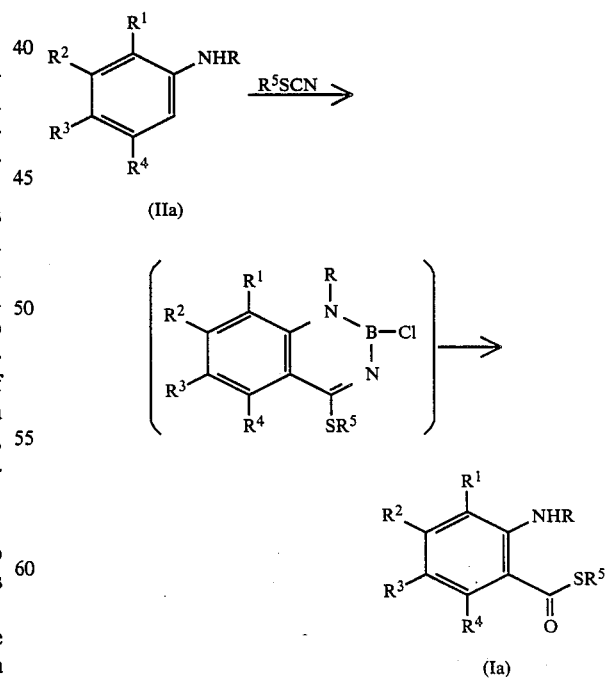

(wherein $R^1$, $R^2$, $R^3$, $R^4$, $R^5$ and R have the same meaning as defined above).

The reaction was performed at room temperature.

TABLE 1

| Ex No | $R^1$ | $R^2$ | $R^3$ | $R^4$ | $R^5$ | R | Time (hr) | m.p. (°C.) or IR (cm$^{-1}$) | Yield (%) |
|---|---|---|---|---|---|---|---|---|---|
| 2 | H | H | H | H | Et | Me | 3 | 1622 | 73 |
| 3 | H | H | H | H | n-Bu | Me | 3 | 1625 | 87 |
| 4 | H | H | H | H | CH$_2$Ph | Me | 3 | 1623 | 87 |
| 5 | H | H | H | H | Me | Et | 15 | 1620 | 79 |
| 6 | H | H | H | H | Me | n-Pr | 15 | 1626 | 76 |
| 7 | H | H | H | H | Me | n-Bu | 15 | 28–29 | 76 |
| 8 | H | H | H | H | Me | CH$_2$Ph | 15 | 47–48 | 91 |
| 9 | H | Cl | H | H | Me | Et | 24 | 83–84 | 45 |
| 10 | H | Cl | H | H | i-Pr | Et | 24 | 1620 | 46 |
| 11 | H | H | Cl | H | Me | Et | 65 | 60–61 | 68 |
| 12 | H | F | H | H | Me | Et | 24 | 51–52 | 54 |
| 13 | H | H | F | H | Me | Et | 65 | 50–51 | 64 |
| 14 | H | Cl | Cl | H | Me | Et | 65 | 84–85 | 21 |
| 15 | H | OMe | H | H | Me | Et | 3 | 55–56 (4-OMe Compd.) | 49 |
|   |   |   |   |   |   |   |   | 1608 (6-OMe Compd.) | 23 |

EXAMPLE 16

To a solution of 1.14 g of N-(1-methyl-4-piperidinyl)aniline in 20 ml of toluene was added 3.6 ml of a solution of 2.04M boron trichloride—toluene and the mixture was refluxed with heating on an oil bath for 2 hr. After cooling, the reaction mixture was mixed with 0.49 ml of methyl thiocyanate and refluxed with heating on an oil bath for 2 hr. After cooling, 20 ml of water was added and the mixture was stirred at 110° C. on an oil bath for 1 hr. The rection mixture was turned to basic conditions with aqueous 2N sodium carbonate and extracted with toluene. The toluene layer was dried over anhydrous magnesium sulfate, chromatographed on a column of 20 g of aluminium oxide for purification, eluted with methylene chloride and concentrated. The crystalline residue (1.35 g) was recrystallized from ether—petroleum ether to give 1.21 g of N-(1-methyl-4-piperidinyl)thioanthranilic acid S-methyl ester melting at 64°–65° C. as yellow crystals.

Yield: 76%

Anal Calcd. for C$_{14}$H$_{20}$ON$_2$S: C, 63.60; H, 7.60; N, 10.60; S, 12.13; Found (%): C, 63.56; H, 7.69; N, 10.57; S, 11.92.

EXAMPLE 17-23

Using the undermentioned starting materials (IIa), the reactions were performed in the same manner as in Example 16, whereby the corresponding objective compounds (Ia) were obtained.

The results are shown in Table 2.

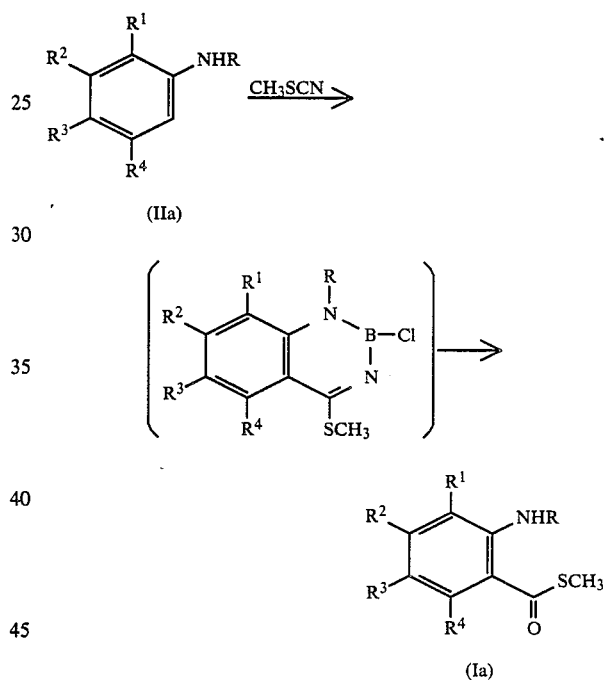

(wherein $R^1$, $R^2$, $R^3$, $R^4$ and R have the same meaning as defined above).

The reaction was performed under refluxing.

TABLE 2

| Ex. No. | $R^1$ | $R^2$ | $R^3$ | $R^4$ | R | Solvent | Time (hr) | m.p. (°C.) | Yield (%) |
|---|---|---|---|---|---|---|---|---|---|
| 17 | H | H | Cl | H | -⟨piperidinyl⟩-N—CH$_3$ | TL | 2 | 81–82 | 80 |
| 18 | H | H | F | H | -⟨piperidinyl⟩-N—CH$_3$ | TL | 2 | 68–69 | 66 |
| 19 | H | H | OMe | H | -⟨piperidinyl⟩-N—CH$_2$Ph | DE | 3 | 111–113 | 76 |

TABLE 2-continued

| Ex. No. | R¹ | R² | R³ | R⁴ | R | Solvent | Time (hr) | m.p. (°C.) | Yield (%) |
|---|---|---|---|---|---|---|---|---|---|
| 20 | H | H | H | H | —N—CH₂Ph (pyrrolidine) | TL | 2 | 187–188* | 81 |
| 21 | H | H | Cl | H | —N—CH₂Ph (pyrrolidine) | TL | 2 | 157–158* | 61 |
| 22 | H | F | H | H | —N—CH₂Ph (pyrrolidine) | TL | 2 | 179–181* | 77 |
| 23 | H | H | OMe | H | —N—CH₂Ph (pyrrolidine) | DE | 3 | 125–127* | 80 |

*HBr salt

EXAMPLE 24

To a solution of 1.69 g of diphenylamine in 10 ml of toluene was added 5.5 ml of a solution of 2.02M boron trichloride—toluene under ice-cooling, and the mixture was refluxed with heating on an oil bath for 1 hr. After ice-cooling, the reaction mixture was mixed with 1 ml of methyl thiocyanate and stirred at room temperature for 16 hr. The reaction mixture was mixed with 20 ml of water and refluxed with heating on an oil bath for 30 min. The insoluble materials were filtered off and the toluene layer was dried over anhydrous magnesium sulfate, chromatographed on a column of silica gel and eluted with toluene. The solvent was concentrated to give 1.03 g of N-phenylthioanthranilic acid S-methyl ester as a yellow oil.

Yield: 42%.

IR (film): 3300, 1628 cm⁻¹.

EXAMPLE 25–26

Using the undermentioned starting materials (IIc), the reactions were performed in the same manner as in Example 24, whereby the corresponding objective compounds (Ic) were obtained.

The results are shown in Table 3.

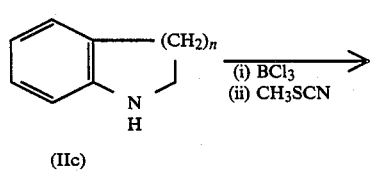

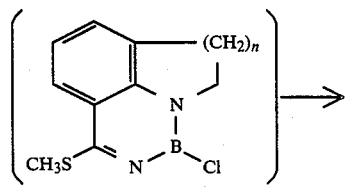

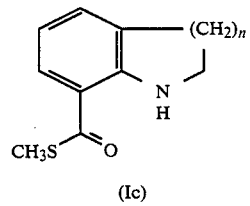

(wherein n is an integer of 1 or 2).

TABLE 3

| Ex. No. | n | Temperature (°C.) | Time (hr) | m.p. (°C.) or IR (film) | Yield (%) |
|---|---|---|---|---|---|
| 25 | 1 | room temperature | 3 | 85–86 | 82 |
| 26 | 2 | room temperature | 3 | 1620 cm⁻¹ | 85 |

EXAMPLE 27

To a solution of 1.35 g of 3,4-dihydro-2H-1,4-benzoxadine in 10 ml of 1,2-dichloroethane was added 5 ml of a solution of 2.02M boron trichloride-1,2-dichloroethane and a mixture solution of 0.82 ml of methyl thiocyanate, 2.9 ml of tri-n-butylamine and 10 ml of 1,2-dichloroethane under ice-cooling. The resulting mixture was stirred at room temperature for 4 hr. The reaction mixture was mixed with 5 ml of 2N HCl and 40 ml of water, and heated at 110° C. on an oil bath to evaporate 1,2-diochloroethane and further stirred for 1 hr. The product was extracted with toluene, dried over anhydrous magnesium sulfate, chromatographed on a column of 10 g of silica gel and eluted with methylene chloride. The solvent was concentrated to give 1.60 g of 3,4-dihydro-2H-1,4-benzoxadin-5-thiocarboxylic acid S-methyl ester as a yellow oil.

Yield: 76%.

IR (film): 3350, 1622 cm⁻¹.

EXAMPLE 28-29

Using the undermentioned starting materials (IIc), the reactions were performed in the same manner as in Example 27, whereby the corresponding objective compounds (Ic) were obtained.

The results are shown in Table 4.

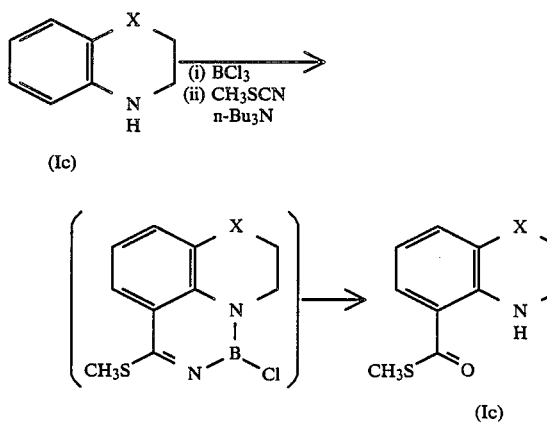

(wherein X has the same meaning as defined above).

TABLE 4

| Ex. No. | X | Temperature (°C.) | Time (hr) | IR (film) cm$^{-1}$ | Yield (%) |
|---|---|---|---|---|---|
| 28 | S | room temperature | 16 | 3325, 1625 | 58 |
| 29 | N—Me | room temperature | 17 | 3340, 1619 | 49 |

EXAMPLE 30

To a solution of 1.67 g of carbazole in 10 ml of toluene was added 5.4 ml of a solution of 2.04M boron trichloride—toluene under ice-cooling, and the mixture was refluxed with heating on an oil bath for 1 hr. After ice-cooling, the mixture was mixed with 1 ml of methyl thiocyanate, stirred at room temperature for 3 hr., mixed with 30 ml of water and refluxed with heating on an oil bath for 1 hr. The product was extracted with toluene, dried over anhydrous magnesium sulfate, chromatographed on a column of 10 g of silica gel and eluted with toluene. The eluate was concentrated to give 2.16 g of the crude crystals. Recrystallization from methylene chloride—ether gave 2.08 g of carbazol-1-thiocarboxylic acid S-methyl ester melting at 122°-123° C. as crystals.

Yield: 86%.

Anal Calcd. (%) for $C_{14}H_{11}ONS$: C, 69.68; H, 4.60; N, 5.81; S, 13.29; Found (%): C, 69.77; H, 4.59; N, 5.79; S, 13.21.

EXAMPLE 31

Using 1.99 g of phenothiazine as a starting material, the reaction was performed in the same manner as in Example 30, whereby 0.798 g of phenothiazin-1-thiocarboxylic acid S-methyl ester was obtained as crystals melting at 92°-93° C.

Yield: 29%.

Anal Calcd. (%) for $C_{14}H_{11}ONS$: C, 61.51; H, 4.06; N, 5.12; S, 23.46; Found (%): C, 61.73; H, 3.92; N, 5.12; S, 23.28.

EXAMPLE 32

To 5.5 ml of a solution of 2.2M boron trichloride-1,2-dichloroethane were added a solution of 941 mg of phenol in 10 ml of 1,2-dichloroethane and 0.82 ml of methyl thiocyanate and 1.33 g of aluminium chloride under ice-cooling. After dissolving aluminium chloride with stirring at room temperature, the mixture was heated at 80° C. on an oil bath for 3 hr. After ice-cooling, the reaction solution was mixed with 6 g of ice and 15 ml of 2N HCl and heated at 110° C. on an oil bath under stirring to evaporate 1,2-dichloroethane and further stirred for 1 hr. After cooling, the mixture was extracted with toluene. The toluene layer was dried over anhydrous magnesium sulfate and chromatographed on a column of 20 g of silica gel for purification. The eluate with toluene was concentrated to give 1.47 g of 2-hydroxythiobenzoic acid S-methyl ester as a colorless oil.

Yield: 88%.

IR (film): 1628 cm$^{-1}$.

EXAMPLE 33-45

Using the undermentioned starting materials (IIb), the reactions were performed in the same manner as in Example 32, whereby the corresponding objective compounds (Ib) were obtained.

The results are shown in Table 5.

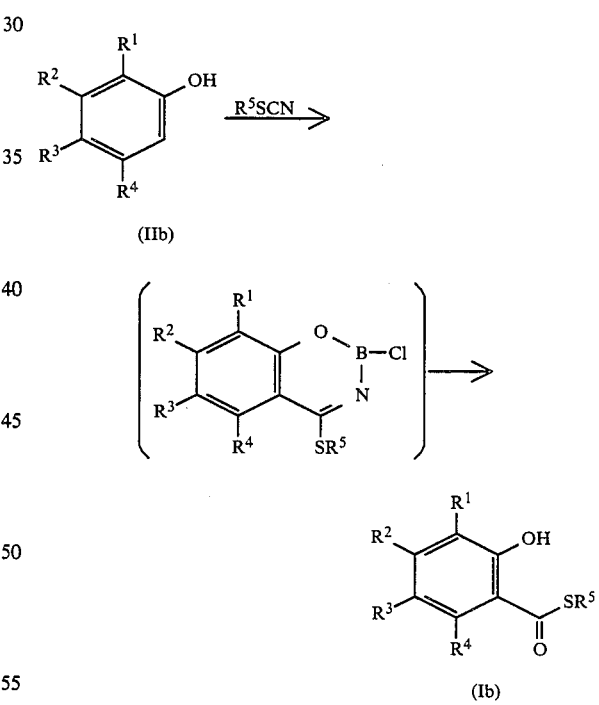

(wherein $R^1$, $R^2$, $R^3$, $R^4$ and $R^5$ have the same meaning as defined above).

The reaction was performed with aluminium chloride as a Lewis acid in 1,2-dichloroethane at 80° C.

TABLE 5

| Ex. No. | $R^1$ | $R^2$ | $R^3$ | $R^4$ | R | Time (hr) | m.p. (°C.) or IR (film) | Yield (%) |
|---|---|---|---|---|---|---|---|---|
| 33 | H | H | H | H | Et | 3 | 1630 cm$^{-1}$ | 75 |
| 34 | H | H | H | H | n-Bu | 3 | 1621 cm$^{-1}$ | 62 |
| 35 | Me | H | H | H | Me | 3 | 1622 cm$^{-1}$ | 79 |
| 36 | H | Me | H | H | Me | 3 | 72-73 | 68 |

TABLE 5-continued

| Ex. No. | $R^1$ | $R^2$ | $R^3$ | $R^4$ | R | Time (hr) | m.p. (°C.) or IR (film) | Yield (%) |
|---|---|---|---|---|---|---|---|---|
| 37 | H | H | Me | H | Me | 3 | 1637 cm$^{-1}$ | 96 |
| 38 | H | Me | Me | H | Me | 3 | 79–80 | 85 |
| 39 | Cl | H | H | H | Me | 64 | 89–90 | 25 |
| 40 | H | Cl | H | H | Me | 16 | 70–71 | 79 |
| 41 | H | H | Cl | H | Me | 64 | 90 | 40 |
| 42 | Cl | Cl | H | H | Me | 64 | 93–94 | 29 |
| 43 | Cl | H | H | OMe | Me | 1 | 98–99 | 41 |
| 44 | H | H | SMe | H | Me | 1 | 45–46 | 13 |
| 45 | Me | H | Cl | OMe | Me | 2 | 100–101 | 21 |

EXAMPLE 46

To a solution of 1.13 ml of boron tribromide in 6 ml of 1,2-dichloroethane were added a solution of 941 mg of phenol in 10 ml of 1,2-dichloroethane, 0.82 ml of methyl thiocyanate and 1.33 g of aluminium chloride under ice-cooling. After dissolving aluminium chloride with stirring at room temperature, the mixture was heated at 80° C. on an oil bath for 3 hr. After ice-cooling, the reaction solution was mixed with 6 g of ice and 15 ml of 2N HCl and heated at 110° C. on an oil bath under stirring to evaporate 1,2-dichloroethane and further stirred for 1 hr. After cooling, the mixture was extracted with toluene. The toluene layer was dried over anhydrous magnesium sulfate and chromatographed on a column of 20 g of silica gel for purification. The eluate with toluene was concentrated to give 1.41 g of 2-hydroxythiobenzoic acid S-methyl ester as a colorless oil.

Yield: 84%

EXAMPLE 47

To 5 ml of a solution of 2.02M boron trichloride—benzene were added a solution of 1.24 g of 3-methoxyphenol in 12 ml of benzene, 0.82 ml of methyl thiocyanate and 1.33 g of aluminium chloride under ice-cooling. After stirring at room temperature for 16 hr., the reaction mixture was cooled with ice water, mixed with 5 g of ice and 15 ml of 2N HCl and stirred with heating at 110° C. on an oil bath to evaporate 1,2-dichloroethane and further stirred for 2 hr. After cooling, the mixture was extracted with toluene. The toluene layer was dried over anhydrous magnesium sulfate and chromatographed on a column of 20 g of silica gel for purification. The product (1.48 g) eluted was recrystallized from ether—petroleum ether to give 1.33 g of 2-hydroxy-4-methoxythiobenzoic acid S-methyl ester melting at 56°–57° C. as white needles.

Yield: 67%

Anal Calcd. (%) for $C_9H_{10}O_3S$: C, 54.52, H, 5.08, S, 16.14; Found (%): C, 54.34, H, 5.15, S, 16.24.

IR (CHCl$_3$): 3220, 1631 cm$^{-1}$.

EXAMPLE 48–51

Using the undermentioned starting materials (IIb), the reactions were performed as in Example 47, whereby the corresponding objective compounds (Ib) were obtained. The results are shown in Table 6.

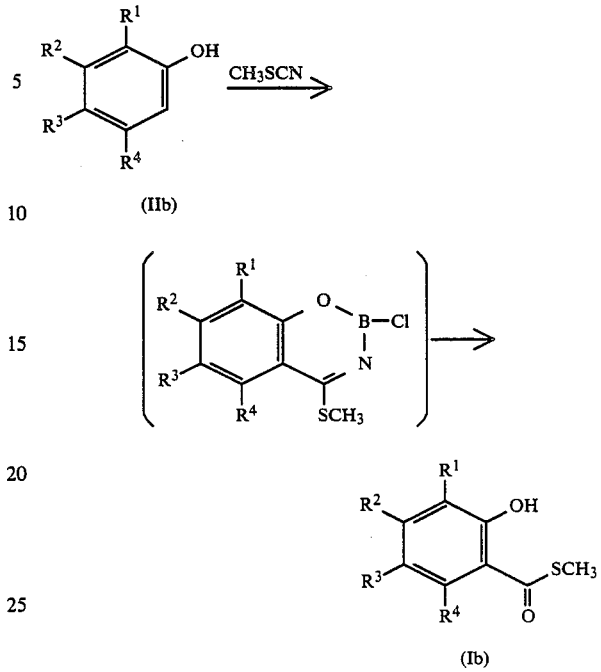

The reaction was performed with aluminium chloride as a Lewis acid at room temperature.

TABLE 6

| Ex. No. | $R^1$ | $R^2$ | $R^3$ | $R^4$ | Solvent | Time (hr) | m.p. (°C.) | Yield (%) |
|---|---|---|---|---|---|---|---|---|
| 48 | H | H | OMe | H | BN | 48 | 65–66 | 74 |
| 49 | Et | H | H | OMe | DE | 16 | 48–49 | 48 |
| 50 | H | OMe | H | OMe | BN | 17 | 111–113 | 57 |
| 51 | H | OMe | H | CH$_2$Ph | DE | 14 | 48–49 | 48 |

EXAMPLE 52

To 5.5 ml of a solution of 2.2M boron trichloride-1,2-dichloroethane were added a solution of 1.44 g of α-naphthol in 30 ml of 1,2-dichloroethane, 0.82 ml of methyl thiocyanate and 1.33 g of aluminium chloride under ice-cooling. After stirring at room temperature for 17 hr., the reaction solution was cooled with ice water and mixed with 15 ml of 2N HCl and 30 ml of water. Then the mixture was heated at 110° C. on an oil bath under stirring to evaporate 1,2-dichloroethane and further stirred for 24 hr. After cooling, the mixture was mixed with 50 ml of methylene chloride under stirring and filtered to remove insoluble materials. The methylene chloride solution was dried over anhydrous magnesium sulfate and the solvent was evaporated. The crude crystals were chromatographed on a column of 20 g of silica gel for purification and 1.51 g of the eluate with toluene was recrystallized from ether—n-hexane to give 1.36 g of 1-hydroxy-2-thionaphthoic acid S-methyl ester at 60°–61° C. as pale yellow crystals.

Yield: 63%

EXAMPLE 53

To 5.5 ml of a solution of 2.2M boron trichloride-1,2-dichloroethane were added a solution of 1.44 g of 62 -naphthol in 30 ml of 1,2-dichloroethane, 0.82 ml of methyl thiocyanate and 1.33 g of aluminium chloride under ice-cooling. After stirring at room temperature for 16 hr., the reaction mixture was cooled with ice water and mixed with 10 g of ice and 40 ml of water, heated at 110° C. on an oil bath under stirring to evaporate 1,2-dichloroethane, and further stirred for 24 hr. After cooling, the resultant was mixed with 50 ml of toluene under stirring and filtered to remove insoluble materials. The toluene solution was dried over anhydrous magnesium sulfate and concentrated. The crude crystals were chromatographed on a column of 30 g of silica gel for purification and 1.19 g of eluate with toluene was recrystallized from ether—n-hexane to give 1.10 g of 2-hydroxy-1-thionaphthoic acid S-methyl ester melting at 111°-112° C. as crystals.

Yield: 51%

REFERENTIAL EXAMPLE 1

A solution consisting of 1.46 g of 2-hydroxythiobenzoic acid methyl ester, 1.1 ml of methyl iodide and 1.2 g of anhydrous potassium carbonate in 20 ml of acetone was stirred at 80° C. on an oil bath for 5 hr. After cooling, the reaction mixture was filtered to remove insoluble materials and concentrated. The residue was chromatographed on a column of 10 g of silica gel for purification. The eluate with methylene chloride was concentrated to give 1.56 g of 2-methoxythiobenzoic acid S-methyl ester as a colorless oil.

Yield: 99%.
IR (film): 1672, 1640 cm$^{-1}$.

REFERENTIAL EXAMPLE 2-5

Using the undermentioned starting materials (Ib), the reactions were performed as in Referential Example 1, whereby the objective compounds (IVb) were obtained.

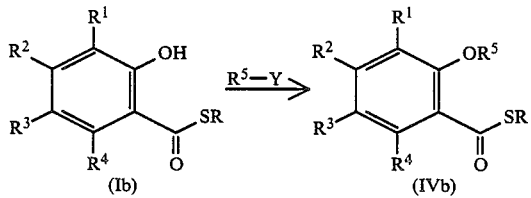

The reaction was performed with anhydrous potassium carbonate as a base in acetone.

The results are shown in Table 7.

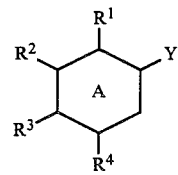
(II)

wherein the ring is benzene ring, $R^1$, $R^2$, $R^3$ and $R^4$ each is hydrogen, halogen, $C_1$-$C_5$ alkyl, $C_1$-$C_5$ alkoxy, $C_1$-$C_5$ alkylthio, $C_6$-$C_{12}$ aryloxy, $C_7$-$C_{15}$ aralkyl, $C_7$-$C_{15}$ aralkoxy or $C_1$-$C_{10}$ acylamino, or ($R^1$ and $R^2$) or ($R_2$ and $R^3$) each taken together may form a condensed benzene ring optionally substituted by halogen, $C_1$-$C_5$ alkyl or $C_1$-$C_5$ alkoxy, Y is hydroxy, amino or NHR, and R is $C_1$-$C_5$ alkyl, $C_7$-$C_{13}$ aralkyl, $C_6$-$C_{12}$ aryl or N-(methyl- or benzyl-substituted aza ($C_3$-$C_7$) cycloalkyl, or R and $R^1$ taken together may form a 5- or 6-membered heterocycle of the formula:

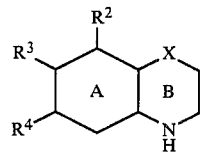
(II')

in which x is a single bond, O, S or N(methyl)- and the B ring which have a condensed benzene, pyridine or cyclohexane ring each optionally substituted by halogen, $C_1$-$C_5$ alkyl or $C_1$-$C_5$ alkoxy, and the A ring, $R^2$, $R^3$, and $R^4$ are the same as defined above, with $C_1$-$C_5$ alkyl thiocyanate, $C_7$-$C_{13}$ aralkyl thiocyanate or $C_6$-$C_{12}$ aryl thiocyanate in a solvent in the presence of a boron trihalide at a temperature of 10° C. to about the boiling point of the solvent; and hydrolyzing the resultant product under acidic conditions at a temperature of 0°-100° C.

2. A process according to claim 1, in which said phenyl compound is represented by the formula:

(IIa)

TABLE 7

| Ref. Ex. No. | $R^1$ | $R^2$ | $R^3$ | $R^4$ | R | $R^5$—Y | Time (hr) | IR (cm$^{-1}$) | Yield (%) |
|---|---|---|---|---|---|---|---|---|---|
| 2 | H | H | H | H | Et | Me$_2$SO$_4$ | 5 | 1675 1632 | 99 |
| 3 | H | H | Me | H | Me | PhCH$_2$Br | 2 | 1678 1634 | 98 |
| 4 | H | Me | H | H | Me | CH$_2$=CH—CH$_2$—Br | 2 | 1672 1632 | 99 |
| 5 | H | H | OMe | H | Me | ◯—CH$_2$—Br | 16 | 1680 1627 | 70 |

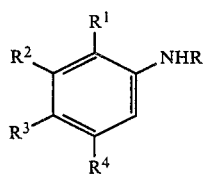

What we claim is:

1. A process for introducing a thiocarboxylic acid ester group at the ortho-position of a phenol or a phenylamine which comprises:

reacting a phenyl compound of the formula:

(wherein R is $C_1$–$C_5$ alkyl, $C_7$–$C_{15}$ aralkyl, $C_6$–$C_{12}$ aryl or N-(methyl- or benzyl-substituted)aza($C_3$–$C_7$)cycloalkyl and $R^1$, $R^2$, $R^3$ and $R^4$ are as defined above).

3. A process according to claim 1, in which said phenyl compound is represented by the formula:

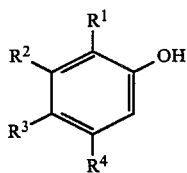
(IIb)

(wherein $R^1$, $R^2$, $R^3$ and $R^4$ are as defined above).

4. A process according to claim 1, in which said phenyl compound is represented by the formula:

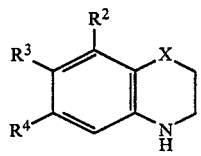
(IIc)

(wherein $R^2$, $R^3$, $R^4$ and X are as defined above).

5. A process according to claim 1, in which said phenyl compound is represented by the formula:

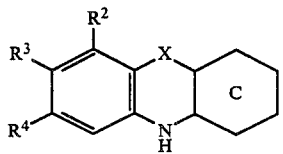

(wherein the ring C is a benzene, pyridine or cyclohexane ring each optionally substituted by halogen, $C_1$–$C_5$ alkyl or $C_1$–$C_5$ alkoxy and $R^2$, $R^3$, $R^4$ and X are as defined above).

6. A process according to claim 3, in which the compound (IIb) is α-naphthol or β-naphthol.

7. A process according to claim 4, in which the compound (IIc) is 1,2,3,4-tetrahydroquinoline, indoline, 2,3-dihydro-4H-1,4-benzothiazine, N-methylbenzopiperazine or 3,4-dihydro-2H-1,4-benzoxazine.

8. A process according to claim 5, in which the compoud (IId) is carbazole or phenothiazine.

9. A process according to claim 1, in which the reaction is carried out in the presence of a Lewis acid.

* * * * *